United States Patent [19]

Dodd

[11] 4,236,032
[45] Nov. 25, 1980

[54] PREPARATION OF 6-T-BUTYL ALKYL-SUBSTITUTED PHENOLS

[75] Inventor: John R. Dodd, Ponca City, Okla.

[73] Assignee: Conoco, Inc., Ponca City, Okla.

[21] Appl. No.: 55,089

[22] Filed: Jul. 5, 1979

[51] Int. Cl.$^3$ ............................................. C07C 37/14
[52] U.S. Cl. .................................... 568/788; 568/793
[58] Field of Search ................................ 568/788, 793

[56] References Cited

U.S. PATENT DOCUMENTS

| 2,802,884 | 8/1957 | D'Alelio | 568/788 |
| 3,382,283 | 5/1968 | Zundel et al. | 568/788 |

FOREIGN PATENT DOCUMENTS

| 692355 | 8/1964 | Canada | 568/788 |

OTHER PUBLICATIONS

Isagulvant et al., "Chem. Abstract," vol. 61, pp. 10611–10612 (1969).
Gakh, "Chem. Abstract," vol. 72, p. 30892w (1969).

Primary Examiner—Werren B. Lone
Attorney, Agent, or Firm—Bayless E. Rutherford, Jr.

[57] ABSTRACT

A process for preparing 6-t-butyl alkylphenols from alkylphenols in high selectivity is disclosed, wherein the starting alkylphenol is a 3-alkylphenol or a 2,3-dialkylphenol and the alkyl group is a $C_1$–$C_6$ primary alkyl. The process comprises reacting a 3-alkylphenol or a 2,3-dialkylphenol, wherein the alkyl group is a $C_1$–$C_6$ primary alkyl, with isobutylene in the presence of a catalyst, which is a sulfonated polystyrene crosslinked with a divinylbenzene, at a temperature of 50° to 90°C.

9 Claims, No Drawings

PREPARATION OF 6-T-BUTYL ALKYL-SUBSTITUTED PHENOLS

FIELD OF THE INVENTION

The invention is in the field of preparing 6-t-butyl-2,3-xylenol, 6-t-butyl-3-cresol and to homologs of these materials wherein the methyl group(s) is replaced by a $C_2$–$C_6$ primary alkyl group.

GENERAL BACKGROUND 6-t-Butyl-2,3-xylenol and 6-t-butyl-3-cresol are useful as antioxidants.

6-t-Butyl-2,3-xylenol can be prepared by butylation of 2,3-xylenol with isobutylene using one of a variety of acidic catalysts such as sulfuric acid and boron trifluoride etherate. The selectivity to the desired product, however, is not particularly good due to the simultaneous production of 4-t-butyl-2,3-xylenol and 4,6-di-t-butyl-2,3-xylenol. The preceding statements apply also to the cresol homolog.

I have found a relatively straight-forward method of preparing 6-t-butyl-2,3-xylenol and 6-t-butyl-3-cresol. The method is also useful for preparing homologs of these materials wherein the methyl group is replaced by a $C_2$–$C_6$ primary alkyl group.

The important features of my process are the use of a specific type of catalyst and a specific temperature range.

BRIEF SUMMARY OF THE INVENTION

Briefly stated, the present invention is directed to a process for preparing 6-t-butyl alkylphenols, wherein the alkylphenol is a 3-alkylphenol or a 2,3-dialkylphenol, wherein the alkyl groups are $C_1$–$C_6$ primary, said process comprising reacting a 3-alkylphenol or a 2,3-dialkylphenol, wherein the alkyl groups are $C_1$–$C_6$ primary, with isobutylene in the presence of an effective amount of a catalyst, which is a sulfonated polystyrene crosslinked with divinylbenzene, at a temperature in the range of 50° to 90° C.

It is understood that the 3-alkylphenol is used to prepare the 6-t-butyl alkylphenol, while the 2,3-dialkylphenol is used to prepare the 6-t-butyl dialkylphenol.

In a preferred embodiment, the process is directed to the preparation of 6-t-butyl-2,3-xylenol and 6-t-butyl-3-cresol from 2,3-xylenol and 3-cresol, respectively. The preparation of 6-t-butyl-2,3-xylenol is a particularly preferred embodiment of my invention.

DETAILED DESCRIPTION

The products prepared by my invention can be represented by the following formulae:

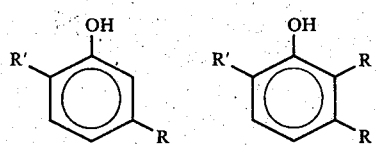

wherein R is a $C_1$–$C_6$ primary alkyl group, but preferably is methyl, and R' is a tertiary-butyl group.

Either 3-alkylphenol or 2,3-dialkylphenol can be used in my process to prepare the respective product. The alkyl group is a $C_1$–$C_6$ primary alkyl, but preferably is methyl.

Isobutylene is used in my process to alkylate the phenolic compounds.

On a molar basis a suitable amount of isobutylene, per mole of phenolic compound, is about 0.5 to about 2. On the same basis, the preferred amount of isobutylene is about 0.7 to about 1.

Suitable catalysts include sulfonated polystyrene resins crosslinked with at least 2 percent of divinylbenzene. The resin should contain at least 2 milliequivalents of acid per gram of dry resin. Preferably, the resin should contain 4 milliequivalents, or higher, of acid per gram of dry resin.

A particularly suitable catalyst is AMBERLYST-15®, which is available from Rohm and Haas Company. This material is a beaded sulfonated polystyrene resin crosslinked with divinylbenzene. The percentage of crosslinking is greater than 20 percent and the resin contains 4.9 milliequivalents of acid per gram of dry resin.

The amount of catalyst is related to the liquid hourly space velocity $$LHSV = \frac{\text{volume of liquid* per hour}}{\text{volume of catalyst}}$$

A suitable range of LHSV is about 0.4 to about 2, preferably about 0.5 to about 1.0. It is understood, of course, that the amount of catalyst is the reciprocal of these values.

While the process can be conducted on a batch basis, preferably it is conducted on a continuous basis. The process can be conducted in a tubular reactor or in a back-mixed reactor. The tubular reaction is preferred.

The temperature at which the reaction is conducted is important in that it has a significant effect on the isomer distribution of the product. Use of a high temperature (e.g. 111° C.) results in a poor selectivity (e.g. 14 percent) of 6-t-butyl-2,3-xylenol. A temperature range of 50° to 90° C. is considered suitable for my process, with the preferred temperature range being 60° to 80° C.

The process is conducted at a pressure in the range of 1 to 200 psig, preferably in the range of 1 to 50 psig.

The process results in a high selectivity of 6-t-butylated product, wherein the term high selectivity refers to at least 85 mole percent based upon the starting substituted phenol.

The desired products can be recovered and purified by any one of many common techniques known to those skilled in the art. Fractional distillation is a particularly good means for recovering and purifying the product.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example illustrates the invention using a continuous tubular reactor. The phenolic mixture used in the feed had the following composition:

| | |
|---|---|
| 2,3-xylenol | 19.05% |
| 2,4-/2,5-xylenol | 34.69% |
| 2,6-xylenol | 9.88% |
| 2,4,6-trimethylphenol | 29.31% |
| 2,3,6-trimethylphenol | 3.53% |
| pentamethylbenzene | 2.89% |

The composition also contained small amounts (less than 0.5 percent) of phenol and cresols. The reactor was a stainless steel continuous tube (57 cm × 1.30 cm i.d.). It was packed with 44 grams of dry AMBERLYST-15 ®.

A feed consisting of 425 grams of the above cresylic acid mixture and 115.2 grams of isobutylene was passed through the reactor containing the catalyst sequentially under the conditions shown in Table I. The product stream was collected in fractions of approximately 20 ml; the fractions were analyzed by gas chromatography. The reactor was operated under a given set of conditions (as specified in Table I) at least as long as required for two successive fractions to show no differences in their gc traces; these fractions were then taken as representative of the particular conditions used. The products of the butylation were then identified using known samples, gas chromatographic analysis, and spectroscopic analysis. The selectivity data reported in Table I was calculated from gas chromatographic analysis of the product stream representative of a given set of conditions.

TABLE 1

PROCESS CONDITIONS AND PRODUCT RESULTS FOR EXAMPLE 1

| Run | T (°C.) | p (a) (psig) | M (b) | LHSV | Conv (c) (IB) | Conv (c) (2,3) | Sel (d) (1) | Sel (d) (2) | Sel (d) (3) | Sel (d) (4) |
|---|---|---|---|---|---|---|---|---|---|---|
| A | 50 | 3 | 0.93 | 0.71 | 99.5 | 80 | 86.6 | 0.0 | 1.1 | 12.2 |
| B | 71 | 3 | 0.93 | 0.88 | 99.7 | 72 | 96.7 | 0.2 | 1.9 | 1.1 |
| C | 90 | 3 | 0.93 | 0.68 | 99.6 | 53 | 92.6 | 4.5 | 2.5 | 0.4 |
| D | 111 | 3 | 0.93 | 0.41 | 97.7 | 62 | 14.0 | 83.3 | 1.6 | 1.1 |

(a) P = Back-pressure on tublar reactor in psig.
(b) M = Moles isobutylene ÷ moles xylenol in feed.
(c) Conv (IB) = Percent conversion of isobutylene.
(c) Conv (2,3) = Percent conversion of 2,3- xylenol.
(d) Sel (1) = Selectivity for 6-t-butyl-2,3-xylenol.
(d) Sel (2) = Selectivity for 5-t-butyl-2,3-xylenol.
(d) Sel (3) = Selectivity for 4-t-butyl-2,3-xylenol.
(d) Sel (4) = Selectivity for 4,6-di-t-butyl-2,3-xylenol.
All calculated selectivities are based on gc* area percentages of these products in the gc* traces of the proxuct streams.

EXAMPLE 2

Run B of Example 1 is repeated except that 3-cresol is substituted for the cresylic acid mixture. The process results in a selectivity of better than 95 percent of 6-t-butyl-3-cresol.

Thus, having described the invention in detail, it will be understood by those skilled in the art that certain variations and modifications may be made without departing from the spirit and scope of the invention as defined herein and in the appended claims.

I claim:

1. A process for preparing 6-t-butyl-3-alkylphenol or 6-t-butyl-2,3-dialkylphenol, said process comprising reacting a 3-alkylphenol or a 2,3-dialkylphenol, respectively, with isobutylene in the presence of an effective amount of a catalyst, which is a sulfonated polystyrene crosslinked with at least 2 percent divinylbenzene, said catalyst containing at least 2 milliequivalents of acid per gram of dry resin, at a temperature of about 50° to 90° C., said process being characterized further in that:
   (a) the alkyl group is a $C_1$-$C_6$ primary alkyl group,
   (b) the amount of isobutylene is in the range of about 0.5 to about 2 moles per mole of phenolic compound,
   (c) the amount of catalyst, expressed as the reciprocal of the LHSV, wherein LHSV = volume of liquid per hour per volume of catalyst, is in the range of about 0.5 to about 2.5, and
   (d) the process results in a product containing at least 85 mole percent 6-t-butyl-3-alkylphenol or 6-t-2,3,-dialkylphenol based upon the amount of 3-alkylphenol or 2,3-dialkylphenol initially present.

2. The process of claim 1 wherein the alkyl group is methyl.

3. The process of claim 2 wherein the amount of isobutylene is in the range of about 0.7 to about 1 mole per mole of phenolic compound.

4. The process of claim 3 wherein the catalyst contains at least 4 milliequivalents of acid per gram of dry resin.

5. The process of claim 4 wherein the amount of catalyst is in the range of about 1.0 to about 2.0.

6. The process of claim 4 wherein the temperature is in the range of about 60° to about 80° C.

7. The process of claim 6 wherein 2,3-xylenol is used to prepare 6-t-butyl-2,3-xylenol.

8. The process of claim 6 wherein 3-cresol is used to prepare 6-t-butyl-3-cresol.

9. The process of claim 2 wherein a cresylic acid mixture feedstock containing about 19 percent 2,3-xylenol is used to prepare 6-t-butyl-2,3-xylenol, said process being characterized further in that:
   (a) the temperature is about 71° C.,
   (b) the mole ratio of isobutylene per mole of 2,3-xylenol is about 0.93,
   (c) the catalyst is crosslinked with greater than 20 percent divinylbenzene and contains 4.9 milliequivalents of acid per gram of dry resin, and
   (d) the amount of catalyst is about 1.14.

* * * * *

UNITED STATES PATENT OFFICE
CERTIFICATE OF CORRECTION

PATENT NO. : 4,236,032
DATED : November 25, 1980
INVENTOR(S) : John R. Dodd

It is certified that error appears in the above—identified patent and that said Letters Patent are hereby corrected as shown below:

Column 2, before line 25, "* includes phenolic compound and isobutylene" was omitted.

Column 3, before line 40, "*gc = gas chromatographic" was omitted.

Signed and Sealed this

Third Day of March 1981

[SEAL]

*Attest:*

RENE D. TEGTMEYER

*Attesting Officer*  Acting Commissioner of Patents and Trademarks